US005503841A

United States Patent [19]

Doyle et al.

[11] Patent Number: 5,503,841
[45] Date of Patent: * Apr. 2, 1996

[54] HUMAN IL-2 AS A VACCINE ADJUVANT

[75] Inventors: Michael V. Doyle, Oakland; Arthur D. Newell, Orinda; Jack H. Nunberg; Thomas J. White, both of Oakland, all of Calif.

[73] Assignee: Cetus Oncology Corporation, Emeryville, Calif.

[*] Notice: The portion of the term of this patent subsequent to Mar. 31, 2009, has been disclaimed.

[21] Appl. No.: 314,975

[22] Filed: Feb. 24, 1989

Related U.S. Application Data

[63] Continuation of Ser. No. 5,926, Jan. 22, 1987, abandoned, which is a continuation-in-part of Ser. No. 856,035, Apr. 25, 1986, abandoned, which is a continuation-in-part of Ser. No. 778,372, Sep. 20, 1985, abandoned.

[51] Int. Cl.$^6$ .............. A61K 38/20; A61K 39/02; A61K 39/12
[52] U.S. Cl. .............. 424/278.1; 424/85.2; 424/207.1; 424/209.1; 424/224.1; 424/241.1; 424/255.1; 424/256.1; 424/261.1; 514/885
[58] Field of Search .............. 424/85.1, 85.2, 424/457, 468, 278.1, 207.1, 209.1, 224.1, 241.1, 255.1, 256.1, 261.1; 530/351, 402; 514/885

[56] References Cited

U.S. PATENT DOCUMENTS

| | | | |
|---|---|---|---|
| 3,674,862 | 7/1972 | Lavender | 424/224.1 |
| 4,196,192 | 4/1980 | Kuo | 424/203.1 |
| 4,604,377 | 8/1986 | Fernandes et al. | 530/351 |
| 4,613,500 | 9/1986 | Suzuki et al. | 424/85.4 |
| 4,780,313 | 10/1988 | Koichiro et al. | 530/351 |
| 4,789,658 | 12/1988 | Yoshimoto et al. | 514/2 |
| 4,840,934 | 6/1989 | Anderson | 514/2 |

OTHER PUBLICATIONS

Merlizzi et al *Eur J Immunopharmac.* vol. 7, 1985, pp. 31–34.

Reed et al *J Immunol* 1984, vol. 133, pp. 3333–3337.

Colizzi, *Inf and Immunity*, vol. 45, 1984, pp. 25–28.

Homberg et al, *J. Immunol.*, vol. 130, 1983, pp. 2644–2650.

Donohue et al, *J Immunol* 130, 1983, 2203–08.

Ralph et al *J. Immunol* vol. 133, 1984, pp. 2442–2445.

Mills, *J Immunol* vol. 125, 1980, pp. 1904–1909.

*Primary Examiner*—Stephen G. Walsh
*Attorney, Agent, or Firm*—Barbara G. McClung; Thomas C. Meyers; Robert P. Blackburn

[57] ABSTRACT

Methods for enhancing the immune response to vaccination in animals, including humans, comprise administering interleukin-2 (IL-2) as part of the vaccination regimen, preferably for 5 to 14 days post-vaccination. In addition, compositions for enhancing the immune response of an animal to a vaccine employ IL-2 as an active ingredient, preferably human IL-2.

16 Claims, 3 Drawing Sheets

```
                                        15              20
 5              10              GlnLeuGlnLeuGlu HisLeuLeuLeuAsp
AlaProThrSerSer SerThrLysLysThr         35              40
                25              TyrLysAsnProLys LeuThrArgMetLeu
LeuGlnMetIleLeu AsnGlyIleAsnAsn         55              60
                45              ThrGluLeuLysHis LeuGlnCysLeuGlu
ThrPheLysPheTyr MetProLysLysAla         75              80
                65              AsnLeuAlaGlnSer LysAsnPheHisLeu
GluGluLeuLysPro LeuGluGluValLeu         95             100
                85              ValIleValLeuGlu LeuLysGlySerGlu
ArgProArgAspLeu IleSerAsnIleAsn        115             120
               105              ThrAlaThrIleVal GluPheLeuAsnArg
ThrThrPheMetCys GluTyrAlaAspGlu        135             140
               125
TrpIleThrPheCys GlnSerIleIleSer ThrLeuThr---
```

FIG. 1

HUMAN IL-2 AS A VACCINE ADJUVANT

CROSS-REFERENCE TO RELATED APPLICATIONS

This application is a continuation of application Ser. No. 005,926, filed Jan. 22, 1987, which is a continuation-in-part of U.S. patent application Ser. No. 856,035 filed Apr. 25, 1986, which is a continuation-in-part of U.S. patent application Ser. No. 778,372 filed Sep. 20, 1985, all abandoned.

BACKGROUND OF THE INVENTION

The invention relates to enhancing the effect of vaccines in animals, such as domestic, sport, or pet species, and humans. More particularly, the invention relates to the use of interleukin-2 (IL-2) as an adjuvant with vaccines.

The use of vaccines to prevent diseases in humans, farm livestock, sports animals and household pets is a common practice, and considerable effort has been, and is being, made to extend this practice to cover a more extensive array of diseases to which these patients are subject. For example, the use of rabies vaccine in animals is by now commonplace, and efforts are being made to obtain suitable vaccines to immunize animals against other diseases.

One problem that frequently is encountered in the course of active immunization is that the antigens used in the vaccine are not sufficiently immunogenic to raise the antibody titer to sufficient levels to provide protection against subsequent challenge or to maintain the potential for mounting these levels over extended time periods. Another problem is that the vaccine may be deficient in inducing cell-mediated immunity which is a primary immune defense against bacterial and viral infection. Notorious among such "weak" animal vaccines are those constituted from inactivated *Haemophilus pleuropneumoniae* (Hpp) (which is associated with respiratory disease in pigs).

In order to obtain a stronger humoral and/or cellular response, it is common to administer the vaccine in a formulation containing an adjuvant (immunopotentiator), a material which enhances the immune response of the patient to the vaccine. The most commonly used adjuvants for vaccines are oil preparations and alum. The mechanisms by which such adjuvants function are not understood, and whether or not a particular adjuvant preparation will be sufficiently effective in a given instance is not predictable.

Accordingly, there is a need for additional effective adjuvant preparations which are suitable for potentiating vaccines for animals in general, including humans and other mammals. It has now been found that human IL-2 (hIL-2) is useful in this regard.

There is considerable background information available with respect to the biological activity of hIL-2. hIL-2 can be obtained from the supernatant of concanavalin-A (ConA) stimulated spleen cells or, presently, using recombinant technology, and has several measurable activities in vitro. First, it is a T-cell growth factor as measured by, for example, thymidine uptake when hIL-2 is added to cultures of cytotoxic or helper T-cell lines. It is mitogenic with respect to adult thymocytes, and stimulates a cytotoxic cell response (e.g., lymphokine-activated-killer (LAK) cell). It has also been shown to replace helper T-cells in athymic murine spleen cell cultures (Watson, J., et al., *Immunological Rev.* (1980) 51:257–278). Specifically, in the presence of IL-2 and antigen, specific T helper cells are generated which are able to contribute to antibody responses. Presumably this occurs because IL-2 is involved in the antigen-dependent maturation of helper T-cells in these nude mouse spleen cultures.

IL-2 has also been shown to directly affect B cells in vitro. Both proliferation and IgM and IgG secretion are enhanced by IL-2 in populations of purified, activated B cells (Mingari, M. C., et al., *Nature* (1984) 312:641; Mittler, R., et al., *J. Immunol.* (1985) 134:2393–2399; Muraguchi, A., et al., *J. Exp. Med.* (1985) 161:181–197).

How these in vitro activities translate into a specific in vivo mechanism for mounting an immune defense is not clear. However, with respect to such in vitro studies, cross-reactivity among species of various IL-2s has been studied. For example, Redelman, D., et al., *J. Immunol. Meth.* (1983) 56:359–370) show that hIL-2 supports activated T lymphocytes derived from rabbit and mouse to approximately the same extent as they are supported by the endogenous forms of IL-2. Ruscetti, F. W., et al., *Blood* (1981) 57:379–393 were the first to demonstrate the ability of hIL-2 to behave as a growth factor, not only for human T-cells, but also peripheral blood lymphocytes or splenocytes from other primates, horse, guinea pig, cat, rat, and mouse. Carter, J., et al., (*Fed. Proc.* (1985) 44:1290) disclose the ability of hIL-2 to enhance the development and maintenance of bovine cytotoxic lymphocytes in vitro.

Doyle, M. V., et al., *J. Bio. Resp. Mod.* (1985) 4:96–109 reports in vitro lymphocyte proliferation studies that compared the activities of native hIL-2 and a recombinant form of IL-2 on human and animal lymphocytes. The native IL-2 and recombinant IL-2 exhibited the same range of activity on animal cells.

Some in vivo data are also available. The activity of IL-2 in vivo has been shown to restore immunocompetence in nude mice in response to heterologous erythrocytes (Stotter, H., et al., *Eur. J. Immunol.* (1980) 10:719–722). There is information concerning cross-species reactivity, as well. Reed, S. G., et al., *J. Immunol.* (1984) 133:3333, disclosed the ability of hIL-2 to reconstitute spleen cell responses in mice infected with a parasitic protozoan, and Farrar, J. J., et al., *Immunol. Rev.* (1982) 63:158, showed that in vivo injection of IL-2 of human origin stimulates the splenic T-cells in nude mice. Fong et al., *Vet. Immuno. & Immunopathol.* (1986) 11:91–100 discloses the response of bovine and porcine peripheral blood mononuclear cells to human rIL-2. Stott et al., *Vet. Immunol. and Immunopathol.* (1986) 13:31–38 disclose that human rIL-2 augments in vitro the blastogenesis of bovine and porcine lymphocytes. Kawamura et al., *J. of Exp. Med.* (1985) 162:381–386 disclose that immunization with antigen and IL-2 in vivo overcomes Ir gene low responsiveness in mice. McFeeters and Nadler, *Fed. Proc.* 45(3) 633 (presented Apr. 13–18, 1986) disclose enhancement of antibody responses to protein antigens by administering rIL-2. Dr. Thompson at the University of Washington is investigating that IL-2 may boost vaccines (Gen. Tech. News, June 1986).

In summary, it is known that IL-2 behaves in some manner in vivo to mediate a successful immune response, including a response to a specific antigen, and in vitro studies have shown that cross-species reactivity of hIL-2 is very diverse (prior in vivo cross-species studies have involved only murine subjects for hIL-2). However, because the mechanism of involvement of hIL-2 in the immune response is not understood, it is not possible to predict the behavior of hIL-2 in boosting a protective immune response to an antigen administered as a vaccine to animals or humans. Accordingly, there is no suggestion in the art that hIL-2 could successfully be used as an adjuvant in vaccines. This is the contribution of the present invention.

SUMMARY OF THE INVENTION

IL-2 is a singularly effective adjuvant in connection with vaccines. Accordingly, in one aspect, the invention relates to a composition for enhancing the immune response of an animal to a vaccine, which composition comprises IL-2. In another aspect, the invention relates to a method of enhancing the immune response of an animal subject, including humans, to a vaccine, which comprises administering to the subject an effective amount of IL-2 as part of the vaccination regimen.

When used as a vaccine adjuvant, hIL-2 is effective on humans as well as animals. Accordingly, another aspect of the invention is a composition for enhancing the immune response of a human to a vaccine, which composition comprises hIL-2. In terms of a method, this aspect of the invention is a method for enhancing the immune response of a human to a vaccine, which method comprises administering hIL-2 to the human as part of the vaccination regimen.

BRIEF DESCRIPTION OF THE DRAWINGS

FIG. 1 shows the amino acid sequence of hIL-2.

DETAILED DESCRIPTION OF THE PREFERRED EMBODIMENTS

A. Definitions

Figure 2A:
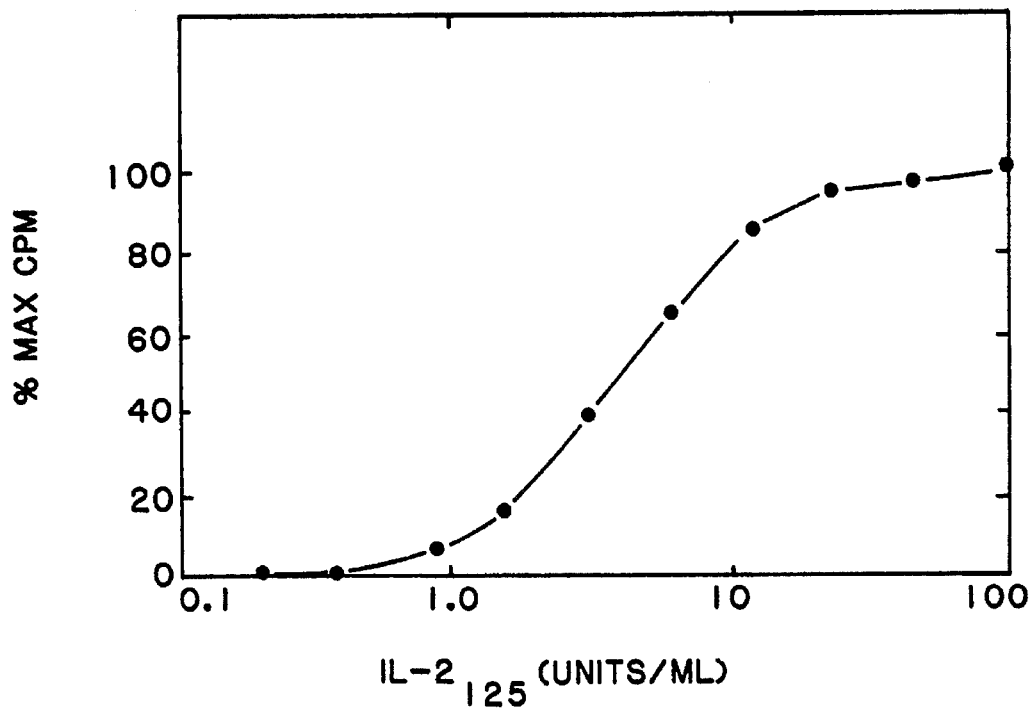
FIGS. 2A and 2B are dose-response curves showing the results of the lymphocyte proliferation tests described in section C.1 of the examples, infra.

As used herein, "IL-2" refers to a polypeptide obtained from tissue cultures or by recombinant techniques exhibiting the spectrum of activities characterizing this protein. The word includes not only human IL-2 (hIL-2), but also other mammalian IL-2 such as, e.g., mouse, rat, rabbit, primate, pig and bovine IL-2. Bovine IL-2 is described by Cerretti et al., *PNAS*, 83:3223–3227 (1986). The term "IL-2" also refers to a protein that is capable of stimulating the proliferation of hIL-2 dependent cytolytic and helper T-cell lines, as set forth in the standard assays of Gillis, S., et al., *J. Immunol.* (1978) 120:2027–2032 and of Watson, J., *J. Exp. Med.* (1979) 150:1510–1519. The amino acid sequence of native hIL-2 is shown in FIG. 1. This primary amino acid sequence may be obtained as the native protein from natural sources or may be recombinantly derived. The recombinant hIL-2 i s preferred herein.

The term "recombinant interleukin-2," designated as IL-2, preferably human IL-2, refers to interleukin-2 having comparable biological activity to native IL-2 prepared by recombinant DNA techniques as described, e.g., by Taniguchi et al., *Nature*, 302:305–310 (1983) and Devos, *Nucleic Acids Research*, 111:4307–4323 (1983). In general, the gene coding for IL-2 is excised from its native plasmid and inserted into a cloning vector to be cloned and then into an expression vector, which i s used to transform a host organism, preferably a microorganism, and most preferably *E. coli*. The host organism expresses the foreign gene to produce IL-2 under expression conditions.

More preferably the IL-2 is a mutein as described in U.S. Pat. No. 4,518,584, in which the cysteine normally occurring at position 125 of the wild-type or native molecular has been replaced by a neutral amino acid such as serine or alanine. Alternatively or conjunctively, the IL-2 mutein may be one as described in copending U.S. application Ser. No. 810,656 filed Dec. 17, 1985, now abandoned the disclosure of which is incorporated herein by reference, in which the methionine normally occurring at position 104 of the wild-type or native molecule has been replaced by a neutral amino acid such as alanine. Finally, the IL-2 employed may have one or more of the first five N-terminal amino acids of the native IL-2 deleted.

Preferably, the IL-2 is a protein produced by a microorganism or by yeast which has been transformed with the human cDNA sequence of IL-2 which encodes a protein with an amino acid sequence at least substantially identical to the amino acid sequence of native human IL-2, including the disulfide bond of the cysteines at positions 58 and 105, and has biological activity which is common to native human IL-2. Substantial identity of amino acid sequences means the sequences are identical or differ by one or more amino acid alterations (additions, substitutions) which do not cause an adverse functional dissimilarity between the synthetic protein and native human IL-2. Examples of IL-2 proteins with such properties include those described by Taniguchi et al., supra; Devos, supra; European Patent Application Nos. 91,539 and 88,195; U.S. Pat. No. 4,518, 584, supra, and copending U.S. application Ser. No. 810,656 filed Dec. 17, 1985, supra. Most preferably, the IL-2 is $ser_{125}$IL-2, des-ala$_1$ser$_{125}$IL-2, des-ala$_1$IL-2, des-ala$_1$ala$_{104}$IL-2, or des-ala$_1$ala$_{104}$ser$_{125}$Il-2, where "des-ala$_1$" indicates that the N-terminal alanyl residue of the IL-2 has been deleted.

The precise chemical structure of the IL-2 herein will depend on a number of factors. As ionizable amino and carboxyl groups are present in the molecule, a particular IL-2 may be obtained as an acidic or basic salt, or in neutral form. All such preparations which retain their bioactivity when placed in suitable environmental conditions are included in the definition of IL-2 herein. Further, the primary amino acid sequence of the IL-2 may be augmented by derivatization using sugar moieties (glycosylation) or by other supplementary molecules such as lipids, phosphate, acetyl groups and the like, more commonly by conjugation with saccharides. Certain aspects of such augmentation are accomplished through post-translational processing systems of the producing host; other such modifications may be introduced in vitro. In any event, such modifications are included in the definition of IL-2 herein so long as the bioactivity of the IL-2 is not destroyed. It is expected, of course, that such modifications may quantitatively or qualitatively affect the bioactivity by either enhancing or diminishing the activity of the IL-2 in the various assays.

As used herein, the term "adjuvant" has its conventional meaning, i.e., the ability to enhance the immune response to a particular antigen. Such ability is manifested by a significant increase in immune-mediated protection. Enhancement of humoral immunity is typically manifested by a significant increase (usually >10%) in the titer of antibody raised to the antigen.

B. General Method

Formulations containing IL-2 for adjuvant purposes are most conveniently administered by intramuscular or subcutaneous injections or as sustained release compositions although other methods of administration are possible. Specific formulations to prevent hydrolysis during digestion would be necessitated for oral formulation, and intravenous injections are generally uneconomic due to the skill level and care required in administration. Therefore, formulations suitable for intramuscular or subcutaneous injection, especially sustained release formulations, are preferred.

Standard formulations are either liquid injectables or solids which can be taken up in suitable liquids as suspensions or solutions for injection. Suitable excipients are, for example, water, saline, dextrose, glycerol, ethanol, and so forth. Nontoxic auxiliary substances, such as wetting agents, buffers, or emulsifiers may also be added. A particularly useful excipient comprises effective amounts of detergents, such as, for example, 0.05% sodium dodecyl sulfate (SDS), to assure solubility and bacteriostasis.

A variety of techniques are known in the art to effect long-term stability and slow release. For example, the stability and half life of IL-2 are enhanced by coupling it to a hydrophilic polymer such as polyethylene glycol (PEG) or a polyoxyethylated polyol as described in copending commonly owned U.S. patent application Ser. No. 866,459, filed May 21, 1986 now abandoned and incorporated herein by reference. The PEG-hIL-2 complex, called "PEGylated" hIL-2, is particularly useful for administering a single sustained action dose of hIL-2.

Another useful IL-2 construct to effect long-term stability and slow release is a succinylated IL-2, as described in copending commonly owned U.S. patent application Ser. No. 903,668 filed Sep. 4, 1986 now abandoned and incorporated herein by reference. Briefly, the succinylation reaction occurs by contacting the IL-2 with succinic anhydride, preferably at pH 5–9 at room temperature in an aqueous solution containing a buffer with a solubilizing agent such as sodium dodecyl sulfate.

Sustained and continuous release formulations are of considerable variety, as is understood by those skilled in the art. An exemplary composition for sustained release parenteral administration is an injectable microcapsule formulation that with a single injection will deliver recombinant hIL-2 or water soluble forms of hIL-2, such as PEGylated or succinylated hIL-2, at a controlled rate, in the range above about $10^3$ and below about $10^6$ units/kg/day, for a duration of 5 to 30 days post vaccination. (Pure hIL-2 has a specific activity of about $3-6 \times 10^6$ U/mg.) The microcapsule formulation is a free-flowing powder consisting of spherical particles 20 to 100 µm in diameter that can be resuspended in an appropriate vehicle and injected intramuscularly or subcutaneously with a conventional hypodermic needle. The microcapsules consist of 0.5% to 5% hIL-2 encapsulated in poly(DL-lactide-co-glycolide) (DL-PLG) excipient, a biodegradable, biocompatible polyester. Alternative standard formulations for sustained release are also usable.

The IL-2 will normally be administered separately from the vaccine, although it may, in some instances, especially in sustained or continuous release forms, be administered in combination with the vaccine. When IL-2 is combined with the vaccine, the composition administered contains an immunogen that is effective in eliciting a specific response to a given pathogen or antigen, a pharmaceutically acceptable vaccine carrier and an immunopotentiating amount of IL-2. A preferred regimen is to administer hIL-2 continuously until 5 to 30 days, preferably 5 to 14 days, post vaccination at levels above about $10^3$ and below about $10^6$ units/kg/day. The term "continuously" is intended to denote true continuous administration, such as is achieved via a sustained release dosage form as well as a multiplicity of intermittent administrations of hIL-2 (or enhanced half-life forms of hIL-2 such as PEGylated or succinylated hIL-2) that provide a pharmacokinetic pattern that mimics that achieved by true continuous administration. Data generated to date using daily intramuscular injections indicate a preferred dose is $10^4$ to $10^5$ units/kg/day. The vaccine will normally be administered per manufacturer's instructions. Other adjuvants may be administered either with the vaccine or together with the IL-2.

The IL-2 will typically be used to enhance the protection afforded by animal or human vaccines that are considered "weak" (i.e., provide diminished protection in terms of level, extent, and/or duration). Examples of such vaccines are bacterins such as Bordetella bacterin, *Escherichia coli* bacterins, Haemophilus bacterins, Leptospirosis vaccines, *Moraxella bovis* bacterin, Pasteurella bacterin and *Vibrio fetus* bacterin and attenuated live or killed virus products such as bovine respiratory disease vaccine (infectious bovine rhinotracheitis, parainfluenza-3, respiratory syncytial virus), bovine virus diarrhea vaccine, equine influenza vaccine, feline leukemia vaccine, feline respiratory disease vaccine (rhinotracheitis-calicipneumonitis viruses), canine parvovirus vaccine, transmissible gastroenteritis vaccine, pseudorabies vaccine, and rabies vaccine.

C. EXAMPLES

The following examples are intended to further support or illustrate but not to limit the invention.

C.1 In Vitro Activity

Figure 2B:
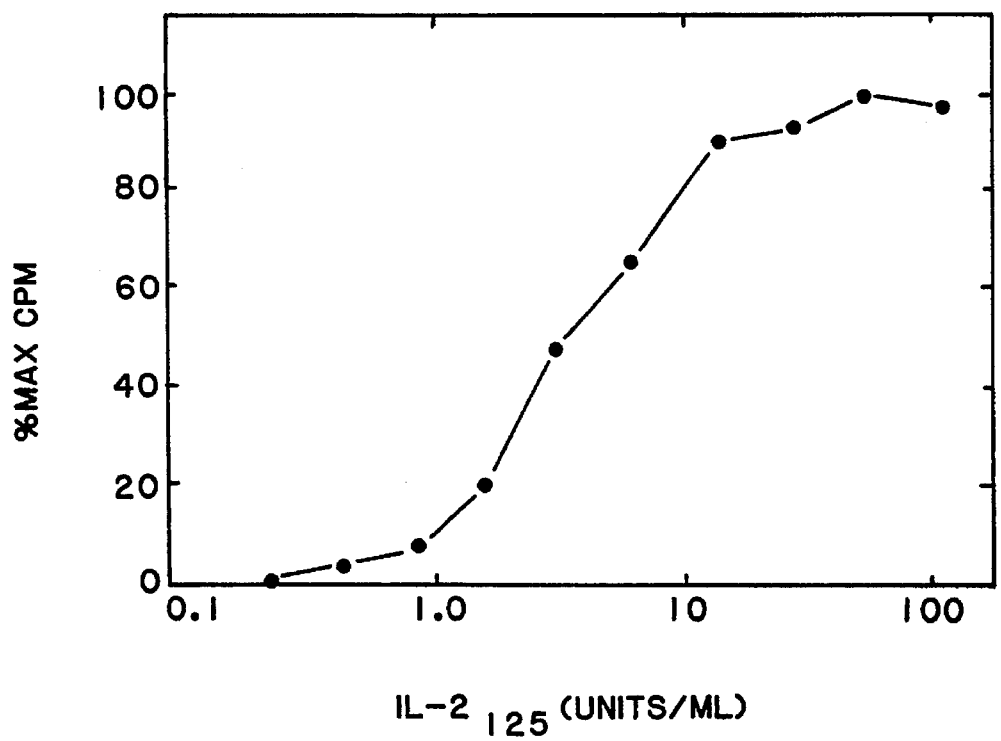

In vitro activity with respect to bovine and porcine peripheral blood mononuclear cells (PBMC) has been shown for recombinant hIL-2 (Fong, Susan, et al., *Vet. Immunol. and Immunopathol.* (1986) 11:91–100, incorporated herein by reference). The hIL-2 used in this work is designated des-alanyl-rIL-$2_{ser125}$, lacks an initial alanine and has a serine rather than a cysteine at position 125. It was shown to be mitogenic for unactivated bovine and porcine PBMC, and to be able to maintain the long-term growth of ConA-activated PBMC from both species. FIGS. 2A and 2B are curves of the dose-response of ConA-activated bovine (2A) and porcine (2B) PBMC to des-alanyl-rIL-$2_{ser125}$. Also, bovine and porcine PBMC preincubated with des-alanyl-rIL-$2_{ser125}$ for 1–5 days showed enhanced cell-mediated cytotoxicity against tumor cell targets.

Figure 3A:
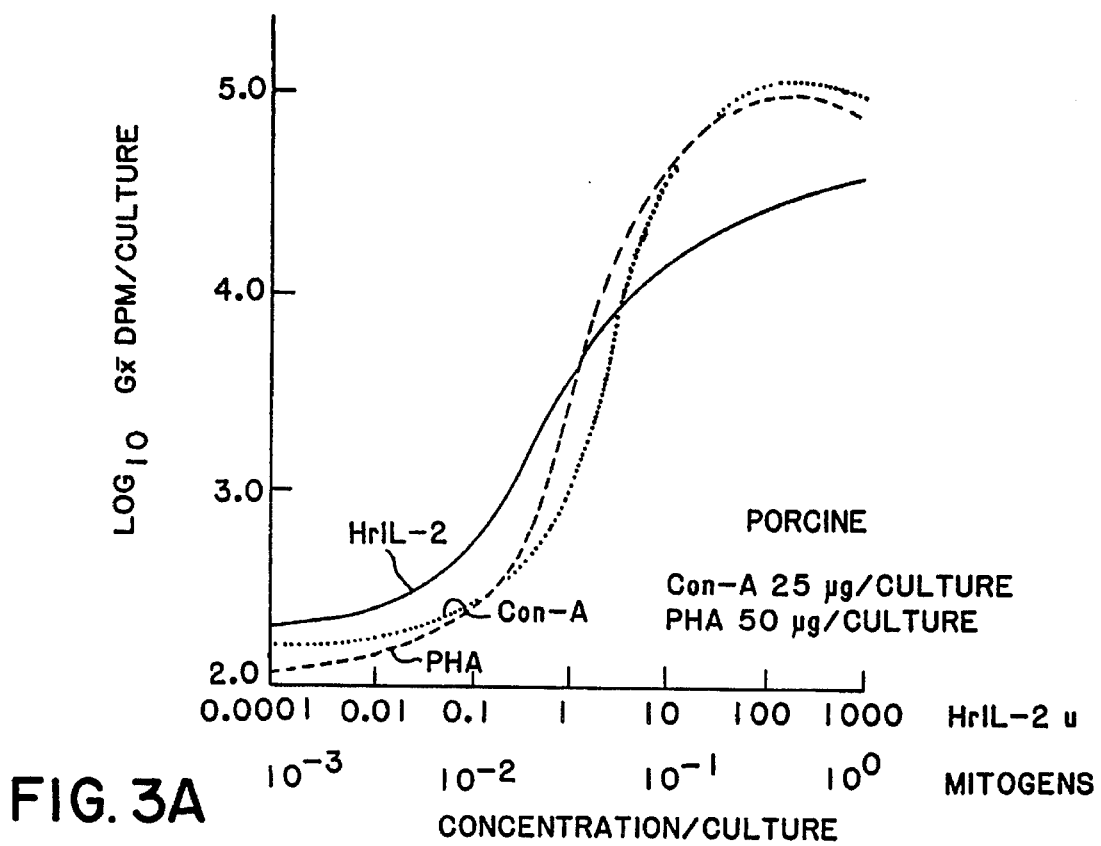
FIG. 3 shows the effect of hIL-2 on blastogenesis of bovine and porcine T-lynmphocytes.
Figure 3B:
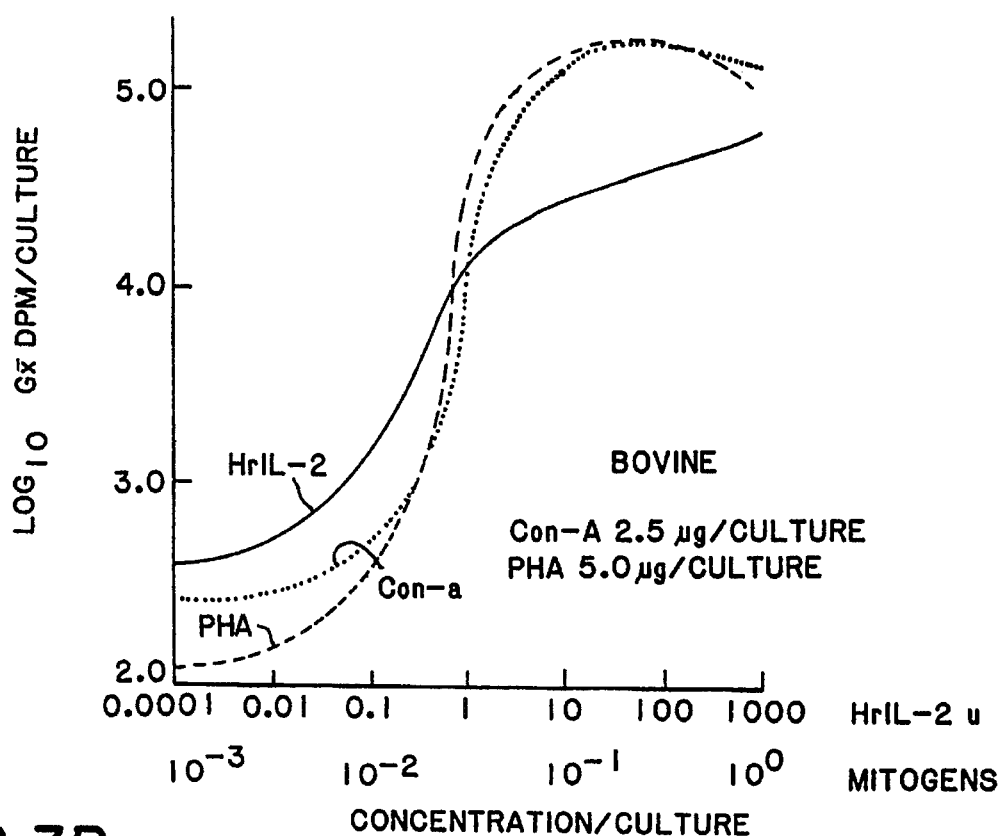

In addition, Stott, J. L., et al., *Vet. Immunol. and Immunopathol.* (1986) 13:31–38 (incorporated herein by reference), have shown that bovine and porcine peripheral blood lymphocytes were responsive to human recombinant IL-2 in lymphocyte blastogenesis assays. Blastogenesis was determined by incorporation of $^3$H-thymidine (18 hr. pulse) in 4-day lymphocyte cultures, and the results were expressed as the $\log_{10}$ of the geometric mean ($G_x$) of disintegrations per minute (DPM)/culture and plotted by nonlinear regression analysis as shown in FIG. 3. Mitogen dilution and concentration of hIL-2 in units are shown on the X-axis. These results show that the effect of hIL-2 on bovine and porcine cells is comparable to that shown by the plant lectins PHA and ConA, which are known to stimulate blastogenesis.

C.2 Effectiveness as an Adjuvant in Porcine Vaccine

Recombinant hIL-2 was shown to enhance the efficacy of an inactivated Hpp bacterin using 12 feeder pigs divided into 6 groups of 2 pigs each. Group 1 was an hIL-2 adjuvant control; group 2 was a bacterin control; group 3 received $10^3$ units hIL-2/kg as a single injection on days 0 and 21; group 4 received 5 daily injections of $10^3$ units/kg each following each vaccination; group 5 received 1 injection of $10^5$ units/kg on days 0 and 21; and group 6 received 5 daily injections of $10^5$ units/kg each following each vaccination.

The pigs in groups 2–6 were administered formalin-inactivated Hpp emulsified in an oil adjuvant intramuscularly in the neck muscles on days 0 and 21. The pigs in all groups were challenged on day 41 intranasally with serotype 1 Hpp and were killed on day 71 and autopsied. Lung area affected was determined visually with particular attention given to lung lesions. The pigs were weighed periodically during the 71 days with weight gain being an indication of general state of health. The results were as follows:

| Group | Autopsy (% Lung Area Affected) | | Average Rate of Body Weight Gain (lb/day) |
| --- | --- | --- | --- |
| | Pig 1 | Pig 2 | Days 41–71 |
| 1 | 24 | 57 | 0.67 |
| 2 | 6 | 100* | * |
| 3 | 25 | 58 | 0.59 |
| 4 | 12 | 12 | 1.89 |
| 5 | 13 | 19 | 0.86 |
| 6 | 0 | 0 | 1.93 |

*pig died 5 days after challenge

As shown by these results the groups that received daily post-vaccination injections of hIL-2 (groups 4 and 6) exhibited substantially higher weight gain post-challenge than did the groups treated otherwise. These results also show a significant reduction of lung pathology in groups 4 and 6, indicating increased protection against challenge provided by the daily administration of hIL-2 in the vaccination regimen. All animals showed high antibody titers against Hpp after challenge.

A second study was carried out to confirm the ability of hIL-2 (des-alanyl-rIL-2$_{ser125}$) to act as an adjuvant to Hpp vaccination. The protocol for the second study was similar to that of the first study described above: animals were vaccinated with/without hIL-2 treatment and subsequently challenged with virulent Hpp. Principal measures of efficacy included clinical signs following infection, weight gain following infection, and the extent of lung involvement at necropsy. The results of this second study are tabulated below.

| Group (N) | Ave. Percent Lung Affected At Necropsy | Ave. Daily Weight Gain (lbs/day) Post-Challenge |
| --- | --- | --- |
| Control (2) | 34 | 0.68 |
| Hpp Alone (3) | 19 | 1.37 |
| Hpp + IL-2 (3) $10^5$ u/kg daily | 01 | 1.86 |
| Hpp + IL-2 (2) $10^4$ u/kg daily | 00 | 1.65 |
| No Challenge (2) | — | 1.82 |

The data from the second study confirm the efficacy observed at $10^5$ u/kg/day hIL-2 in the first study and extend these findings to the lower dose of $10^4$ u/kg/day. Protection at an IL-2 dose of $10^4$ u/kg/day was comparable to that observed at the higher dose.

C.3 Effectiveness as an Adjuvant in Dogs

Dogs were injected with keyhole limpet hemocyanin (KLH) at the time of initial hIL-2 treatment and 7 days subsequently at the start of 5 days of (daily) hIL-2 treatment. Enzyme-linked immunoabsorbent assays (ELISAs) were performed on sera taken from the dogs to measure antibody response to KLH. A significant, dose-dependent increase in IgG antibody against KLH was observed in the IL-2 treated dogs. The increase was specific to the KLH immunogen used.

C.4 Effectiveness as an Adjuvant in Mice

The SAD strain of attenuated live rabies virus adapted to PK-2A cells was inactivated using binary ethylenimine in a final concentration of 0.01M solution to obtain a rabies vaccine. Sixteen Swiss white mice per group were each vaccinated intraperitoneally with 0.5 ml of undiluted, 1:5 diluted, 1:25 diluted or 1:125 diluted concentrations of the rabies vaccine in minimal Eagle's medium (a standard cell culture salt solution). Two doses of vaccine were given to each mouse one week apart.

Each vaccinated mouse was injected subcutaneously with 1 μg hIL-2 diluted with phosphate buffered saline per gram of mouse two times daily for five days starting on the day the mice were vaccinated. The IL-2 injections were also repeated two times daily for five days following the second vaccination.

One week after the second vaccination all the vaccinated mice were challenged by intracranial (IC) inoculation of a CVS strain virulent rabies virus propagated in BHK-21 cells using a dilution that would approximate 20 to 30 mouse LD-50 of virus in 0.03 ml. As a further step to determine more precisely the actual challenge dose, a group of 16 mice were inoculated with the challenge pool. Groups of 10 mice each were also inoculated with a 1:10 and 1:100 dilution of this pool. All inoculations were IC using 0.03 ml inoculums.

All mice were observed daily and signs of rabies or death were recorded. Deaths within 24 hours were discarded as not significant. Observations were made for 12 days post-challenge.

Evaluation of the results of challenge of the vaccinated mice was accomplished using a modification of the volumetric method described in NIH Test for Potency, "Laboratory Techniques in Rabies", Ch. 33, WHO (1973). The simultaneous titration of the CVS rabies challenge virus showed that the vaccinated animals were challenged with 35 mouse LD-50 of virus.

The results of the rabies challenge on the vaccinated mice are summarized below:

| Dilution of Vaccine | Vaccine Only No. Deaths/ No. Vacc. | Vaccine + IL-2 No. Deaths/No. Vacc. & Treated |
| --- | --- | --- |
| Undiluted | 16/16 | 0/15* |
| 1:5 | 15/16 | 5/16 |
| 1:25 | 15/15* | 13/14* |
| 1:125 | 16/16 | 16/16 |

*While 16 mice were vaccinated in each group, the difference reflects 24-hour post-challenge deaths.

As can be seen from the table, despite the poor potency of the rabies vaccine employed, mice receiving the IL-2 plus the lowest dilutions of vaccine showed significant resistance to CVS rabies challenge. This indicates that IL-2 can modify the immune response to allow for production of antibodies against even poor antigens if adequate vaccine is present. Moreover, the effect observed is not due to the IL-2 alone, because at the highest vaccine dilutions of 1:25 and 1:125, the same amount of IL-2 was administered as with the lowest dilutions.

Modifications of the above described modes of carrying out the invention that are obvious to those of skill in the fields of medicine, immunology, pharmacology, and related fields are intended to be within the scope of the following claims.

What is claimed is:

1. A method of enhancing the immune response of a subject animal to an immunoprophylactic, infectious disease vaccine comprising administering an effective amount of interleukin-2 (IL-2) to the subject as part of the immunoprophylactic vaccination regimen before the infection.

2. The method of claim 1 wherein the IL-2 is human IL-2.

3. The method of claim 2 wherein the human IL-2 is des-alanyl-rIL-$2_{ser125}$.

4. The method of claim 2 wherein the human IL-2 is a water soluble form of human IL-2.

5. The method of claim 4 wherein the water soluble form of human IL-2 is PEGylated human IL-2 or succinylated human IL-2.

6. The method of claim 1 wherein the IL-2 is in the form of a continuous release formulation.

7. The method of claim 1 wherein the IL-2 is in the form of a single sustained action formulation.

8. The method of claim 1 wherein the vaccine is an *Escherichia coli* bacterin, Haemophilus bacterin, Pasteurella bacterin, *Vibrio fetus* bacterin, transmissible gastroenteritis vaccine, equine influenza vaccine, feline leukemia vaccine, rabies vaccine, or pseudorabies vaccine.

9. The method of claim 1 wherein the IL-2 is administered subsequent to the administration of the vaccine.

10. The method of claim 6 wherein the IL-2 is administered continuously at a rate of above about $10^3$ and below about $10^6$ units/kg/day for about 5 to 30 days post-vaccination.

11. A method for enhancing the immune response of a human to an immunoprophylactic, infectious disease vaccine, which method comprises administering an effective amount of human interleukin-2 (hIL-2) to the human as part of the immunoprophylactic vaccination regimen before the infection.

12. The method of claim 11 wherein the hIL-2 is a water-soluble form of hIL-2.

13. The method of claim 12 wherein the hIL-2 is PEGylated or succinylated IL-2.

14. The method of claim 11 wherein the hIL-2 is des-alanyl-rIL-$2_{ser125}$.

15. The method of claim 11 wherein the hIL-2 is in the form of a continuous release formulation.

16. The method of claim 11 wherein the hIL-2 is in the form of a single sustained action formulation.

* * * * *